United States Patent
Rashbaum et al.

(10) Patent No.: US 8,771,284 B2
(45) Date of Patent: Jul. 8, 2014

(54) INTERVERTEBRAL DISC PROSTHESIS AND INSTRUMENTATION FOR INSERTION OF THE PROSTHESIS BETWEEN THE VERTEBRAE

(75) Inventors: Ralph Rashbaum, Plano, TX (US); Kee D. Kim, Davis, CA (US); Hyun Bae, Santa Monica, CA (US); Jean-Paul Steib, Strasbourg (FR)

(73) Assignee: LDR Medical, Rosières Près Troyes (FR)

( * ) Notice: Subject to any disclaimer, the term of this patent is extended or adjusted under 35 U.S.C. 154(b) by 0 days.

(21) Appl. No.: 13/620,797

(22) Filed: Sep. 15, 2012

(65) Prior Publication Data

US 2013/0013006 A1 Jan. 10, 2013

Related U.S. Application Data

(62) Division of application No. 11/362,253, filed on Feb. 24, 2006.

(30) Foreign Application Priority Data

Nov. 30, 2005 (FR) ..................................... 05 12133

(51) Int. Cl.
*A61B 17/17* (2006.01)
*A61B 17/58* (2006.01)
*A61B 17/60* (2006.01)
*A61F 2/00* (2006.01)
*A61F 2/44* (2006.01)
*A61F 2/30* (2006.01)
*A61F 2/46* (2006.01)

(52) U.S. Cl.
CPC ..... *A61F 2/4425* (2013.01); *A61F 2002/30369* (2013.01); *A61F 2002/4628* (2013.01); *A61F 2002/4627* (2013.01); *A61F 2002/30601* (2013.01); *A61F 2002/30884* (2013.01); *A61F 2002/30365* (2013.01); *A61F 2230/0069* (2013.01); *A61F 2002/30512* (2013.01); *A61F 2002/30662* (2013.01); *A61F 2/4611* (2013.01); *A61F 2002/30904* (2013.01); *A61F 2002/30841* (2013.01); *A61F 2002/4622* (2013.01); *A61F 2002/30616* (2013.01); *A61F 2002/30878* (2013.01); *A61F 2220/0025* (2013.01); *A61F 2002/443* (2013.01); *A61F 2002/30649* (2013.01); *A61F 2220/0033* (2013.01); *A61F 2002/30235* (2013.01); *Y10S 606/914* (2013.01)

USPC ........................... 606/99; 606/86 A; 606/914

(58) Field of Classification Search
USPC ......................................... 606/99, 86 A, 914
See application file for complete search history.

(56) References Cited

U.S. PATENT DOCUMENTS

| | | |
|---|---|---|
| 3,374,786 A | 3/1968 | Callender et al. |
| 3,791,380 A | 2/1974 | Dawidowski |
| 3,892,232 A | 7/1975 | Neufeld |
| 4,009,712 A | 3/1977 | Burstein et al. |
| 4,135,506 A | 1/1979 | Ulrich |
| 4,175,555 A | 11/1979 | Herbert |
| 4,185,762 A | 1/1980 | Froehlich |
| 4,237,875 A | 12/1980 | Termanini |
| 4,379,451 A | 4/1983 | Getscher |
| 4,409,974 A | 10/1983 | Freedland |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,657,001 A | 4/1987 | Fixel |
| 4,664,305 A | 5/1987 | Blake, III et al. |
| 4,721,103 A | 1/1988 | Freedland |
| 4,759,352 A | 7/1988 | Lozier |
| 4,787,378 A | 11/1988 | Sodhi |
| 4,790,303 A | 12/1988 | Steffee |
| 4,791,918 A | 12/1988 | Von Hasselbach |
| 4,898,156 A | 2/1990 | Gatturna et al. |
| 4,946,468 A | 8/1990 | Li |
| 4,964,403 A | 10/1990 | Karas et al. |

| | | | | | | |
|---|---|---|---|---|---|---|
| 4,968,315 A | 11/1990 | Gatturna | | 6,447,544 B1 | 9/2002 | Michelson |
| 4,969,887 A | 11/1990 | Sodhi | | 6,447,546 B1 | 9/2002 | Bramlet et al. |
| 4,973,332 A | 11/1990 | Kummer | | 6,485,517 B1 | 11/2002 | Michelson |
| 4,973,333 A | 11/1990 | Treharne | | 6,500,205 B1 | 12/2002 | Michelson |
| 5,002,550 A | 3/1991 | Li | | 6,540,753 B2 | 4/2003 | Cohen |
| 5,007,910 A | 4/1991 | Anapliotis et al. | | 6,558,423 B1 | 5/2003 | Michelson |
| 5,032,125 A | 7/1991 | Durham et al. | | 6,558,424 B2 | 5/2003 | Thalgott |
| 5,041,114 A | 8/1991 | Chapman et al. | | 6,565,605 B2 | 5/2003 | Goble et al. |
| 5,041,116 A | 8/1991 | Wilson | | 6,607,530 B1 | 8/2003 | Carl et al. |
| 5,046,513 A | 9/1991 | Gatturna et al. | | 6,648,893 B2 | 11/2003 | Dudasik |
| 5,057,103 A | 10/1991 | Davis | | 6,679,887 B2 | 1/2004 | Nicholson et al. |
| 5,062,851 A | 11/1991 | Branemark | | 6,709,458 B2 | 3/2004 | Michelson |
| 5,087,266 A | 2/1992 | Connell et al. | | 6,716,247 B2 | 4/2004 | Michelson |
| 5,098,433 A | 3/1992 | Freedland | | 6,723,128 B2 | 4/2004 | Uk |
| 5,116,336 A | 5/1992 | Frigg | | 6,749,636 B2 | 6/2004 | Michelson |
| 5,129,901 A | 7/1992 | Decoste | | 6,770,096 B2 | 8/2004 | Bolger et al. |
| 5,176,681 A | 1/1993 | Lawes et al. | | 6,793,679 B2 | 9/2004 | Michelson |
| 5,192,303 A | 3/1993 | Gatturna et al. | | 6,805,714 B2 | 10/2004 | Sutcliffe |
| 5,207,679 A | 5/1993 | Li | | 6,808,537 B2 | 10/2004 | Michelson |
| 5,217,486 A | 6/1993 | Rice et al. | | 6,835,206 B2 | 12/2004 | Jackson |
| 5,234,447 A | 8/1993 | Kaster et al. | | 6,849,093 B2 | 2/2005 | Michelson |
| 5,242,448 A | 9/1993 | Pettine et al. | | 6,890,355 B2 | 5/2005 | Michelson |
| 5,258,009 A | 11/1993 | Conners | | 6,902,580 B2 | 6/2005 | Fallin et al. |
| 5,300,074 A | 4/1994 | Frigg | | 6,916,340 B2 | 7/2005 | Metzger et al. |
| 5,324,292 A | 6/1994 | Meyers | | 6,923,811 B1 | 8/2005 | Carl et al. |
| 5,342,394 A | 8/1994 | Matsuno et al. | | 6,923,830 B2 | 8/2005 | Michelson |
| 5,356,410 A | 10/1994 | Pennig | | 6,936,071 B1 | 8/2005 | Marnay et al. |
| 5,356,413 A | 10/1994 | Martins et al. | | 6,955,691 B2 | 10/2005 | Chae et al. |
| 5,372,599 A | 12/1994 | Martins | | 6,962,606 B2 | 11/2005 | Michelson |
| 5,417,692 A | 5/1995 | Goble et al. | | 6,972,019 B2 | 12/2005 | Michelson |
| 5,417,712 A | 5/1995 | Whittaker et al. | | 6,972,035 B2 | 12/2005 | Michelson |
| 5,429,641 A | 7/1995 | Gotfried | | 6,981,975 B2 | 1/2006 | Michelson |
| 5,437,674 A | 8/1995 | Worcel et al. | | 6,984,234 B2 | 1/2006 | Bray |
| 5,443,514 A | 8/1995 | Steffee | | 7,001,385 B2 | 2/2006 | Bonutti |
| 5,456,721 A | 10/1995 | Legrand | | 7,008,453 B1 | 3/2006 | Michelson |
| 5,458,601 A | 10/1995 | Young, Jr. et al. | | 7,033,394 B2 | 4/2006 | Michelson |
| 5,472,452 A | 12/1995 | Trott | | 7,041,135 B2 | 5/2006 | Michelson |
| 5,478,342 A | 12/1995 | Kohrs | | 7,041,136 B2 | 5/2006 | Goble et al. |
| 5,489,210 A | 2/1996 | Hanosh | | 7,063,701 B2 | 6/2006 | Michelson |
| 5,507,754 A | 4/1996 | Green et al. | | 7,063,702 B2 | 6/2006 | Michelson |
| 5,522,845 A | 6/1996 | Wenstrom, Jr. | | 7,066,961 B2 | 6/2006 | Michelson |
| 5,522,899 A | 6/1996 | Michelson | | 7,074,237 B2 | 7/2006 | Goble et al. |
| 5,531,792 A | 7/1996 | Huene | | 7,090,698 B2 | 8/2006 | Goble et al. |
| 5,534,004 A | 7/1996 | Santangelo | | 7,094,239 B2 | 8/2006 | Michelson |
| 5,549,617 A | 8/1996 | Green et al. | | 7,112,206 B2 | 9/2006 | Michelson |
| 5,554,191 A | 9/1996 | Lahille et al. | | 7,118,579 B2 | 10/2006 | Michelson |
| 5,562,689 A | 10/1996 | Green et al. | | 7,118,598 B2 | 10/2006 | Michelson |
| 5,571,104 A | 11/1996 | Li | | 7,128,760 B2 | 10/2006 | Michelson |
| 5,571,189 A | 11/1996 | Kuslich | | 7,128,761 B2 | 10/2006 | Kuras et al. |
| 5,578,035 A | 11/1996 | Lin | | 7,147,665 B1 | 12/2006 | Bryan et al. |
| 5,591,168 A | 1/1997 | Judet et al. | | 7,163,561 B2 | 1/2007 | Michelson |
| 5,593,409 A | 1/1997 | Michelson | | 7,179,294 B2 | 2/2007 | Eisermann et al. |
| 5,609,635 A | 3/1997 | Michelson | | 7,211,112 B2 | 5/2007 | Baynham et |
| 5,613,974 A | 3/1997 | Andreas et al. | | 7,217,291 B2 | 5/2007 | Zucherman et al. |
| 5,620,012 A | 4/1997 | Benderev et al. | | 7,217,292 B2 | 5/2007 | Ralph et al. |
| 5,643,321 A | 7/1997 | McDevitt | | 7,217,293 B2 | 5/2007 | Branch, Jr. |
| 5,655,698 A | 8/1997 | Yoon et al. | | 7,223,289 B2 | 5/2007 | Trieu et al. |
| 5,683,464 A | 11/1997 | Wagner et al. | | 7,232,463 B2 | 6/2007 | Falahee |
| 5,702,449 A | 12/1997 | McKay | | 7,232,464 B2 | 6/2007 | Mathieu et al. |
| 5,766,253 A | 6/1998 | Brosnahan, III | | 7,326,248 B2 | 2/2008 | Michelson |
| 5,800,547 A | 9/1998 | Schafer et al. | | 7,326,250 B2 | 2/2008 | Beaurain et al. |
| 5,800,550 A | 9/1998 | Sertich | | 7,410,501 B2 | 8/2008 | Michelson |
| 5,807,403 A | 9/1998 | Beyar et al. | | 7,431,735 B2 | 10/2008 | Liu et al. |
| 5,895,427 A | 4/1999 | Kuslich et al. | | 7,435,262 B2 | 10/2008 | Michelson |
| 5,968,098 A | 10/1999 | Winslow | | 7,442,209 B2 | 10/2008 | Michelson |
| 5,980,522 A | 11/1999 | Koros et al. | | 7,445,635 B2 | 11/2008 | Fallin et al. |
| 6,066,175 A | 5/2000 | Henderson et al. | | 7,445,636 B2 | 11/2008 | Michelson |
| 6,099,531 A | 8/2000 | Bonutti | | 7,455,692 B2 | 11/2008 | Michelson |
| 6,102,950 A | 8/2000 | Vaccaro | | 7,465,317 B2 | 12/2008 | Malberg et al. |
| 6,129,763 A | 10/2000 | Chauvin et al. | | 7,481,840 B2 | 1/2009 | Zucherman et al. |
| 6,214,050 B1 | 4/2001 | Huene | | 7,494,507 B2 | 2/2009 | Dixon et al. |
| 6,241,769 B1 | 6/2001 | Nicholson et al. | | 7,494,508 B2 | 2/2009 | Zeegers |
| 6,287,308 B1 | 9/2001 | Betz et al. | | 7,503,933 B2 | 3/2009 | Michelson |
| 6,302,914 B1 | 10/2001 | Michelson | | 7,517,363 B2 | 4/2009 | Rogers et al. |
| 6,319,257 B1 * | 11/2001 | Carignan et al. ............... 606/99 | | 7,540,882 B2 | 6/2009 | Michelson |
| 6,342,074 B1 | 1/2002 | Simpson | | 7,566,345 B1 | 7/2009 | Fallin et al. |
| 6,371,987 B1 | 4/2002 | Weiland et al. | | 7,575,599 B2 | 8/2009 | de Villiers et al. |
| 6,419,703 B1 | 7/2002 | Fallin et al. | | 7,575,600 B2 | 8/2009 | Zucherman et al. |
| 6,423,063 B1 | 7/2002 | Bonutti | | 7,588,590 B2 | 9/2009 | Chervitz et al. |

| | | | | | |
|---|---|---|---|---|---|
| 7,591,851 B2 | 9/2009 | Winslow et al. | 8,066,749 B2 | 11/2011 | Winslow et al. |
| 7,594,931 B2 | 9/2009 | Louis et al. | 8,070,816 B2 | 12/2011 | Taylor |
| 7,594,932 B2 | 9/2009 | Aferzon et al. | 8,070,819 B2 | 12/2011 | Aferzon et al. |
| 7,601,170 B2 | 10/2009 | Winslow et al. | 8,075,593 B2 | 12/2011 | Hess |
| 7,608,107 B2 | 10/2009 | Michelson | 8,075,618 B2 | 12/2011 | Trieu et al. |
| 7,611,538 B2 | 11/2009 | Belliard et al. | 8,075,621 B2 | 12/2011 | Michelson |
| 7,618,453 B2 | 11/2009 | Goble et al. | 8,114,082 B2 | 2/2012 | Boyajian et al. |
| 7,618,455 B2 | 11/2009 | Goble et al. | 8,257,439 B2 | 9/2012 | Zeegers |
| 7,618,456 B2 | 11/2009 | Mathieu et al. | 8,267,999 B2 | 9/2012 | Beaurain et al. |
| 7,621,955 B2 | 11/2009 | Goble et al. | 8,388,684 B2 | 3/2013 | Bao et al. |
| 7,621,956 B2 | 11/2009 | Paul et al. | 8,439,931 B2 | 5/2013 | Dinville |
| 7,621,958 B2 | 11/2009 | Zdeblick et al. | 2002/0035400 A1 | 3/2002 | Bryan et al. |
| 7,632,282 B2 | 12/2009 | Dinville | 2002/0040243 A1 | 4/2002 | Attali et al. |
| 7,637,951 B2 | 12/2009 | Michelson | 2002/0161444 A1 | 10/2002 | Choi |
| 7,637,954 B2 | 12/2009 | Michelson | 2002/0165613 A1 | 11/2002 | Lin et al. |
| 7,641,690 B2 | 1/2010 | Abdou | 2002/0193880 A1 | 12/2002 | Fraser |
| 7,655,027 B2 | 2/2010 | Michelson | 2003/0069586 A1 | 4/2003 | Errico et al. |
| 7,658,766 B2 | 2/2010 | Melkent et al. | 2003/0074075 A1 | 4/2003 | Thomas, Jr. et al. |
| 7,682,396 B2 | 3/2010 | Beaurain et al. | 2003/0093153 A1 | 5/2003 | Banick et al. |
| 7,695,516 B2 | 4/2010 | Zeegers | 2003/0135279 A1 | 7/2003 | Michelson |
| 7,695,517 B2 | 4/2010 | Benzel et al. | 2003/0187436 A1 | 10/2003 | Bolger et al. |
| 7,708,776 B1 | 5/2010 | Blain et al. | 2003/0195514 A1 | 10/2003 | Trieu et al. |
| 7,717,959 B2 | 5/2010 | William et al. | 2004/0010312 A1 | 1/2004 | Enayati |
| 7,727,280 B2 | 6/2010 | McLuen | 2004/0024406 A1 | 2/2004 | Ralph et al. |
| 7,749,252 B2 | 7/2010 | Zucherman et al. | 2004/0153157 A1 | 8/2004 | Keller |
| 7,749,274 B2 | 7/2010 | Razian | 2004/0158254 A1 | 8/2004 | Eisermann |
| 7,753,937 B2 | 7/2010 | Chervitz et al. | 2004/0158328 A1 | 8/2004 | Eisermann |
| 7,771,473 B2 | 8/2010 | Thramann | 2004/0210219 A1 | 10/2004 | Bray |
| 7,771,475 B2 | 8/2010 | Michelson | 2004/0210313 A1 | 10/2004 | Michelson |
| 7,771,478 B2 | 8/2010 | Navarro et al. | 2004/0254643 A1 | 12/2004 | Jackson |
| 7,776,090 B2 | 8/2010 | Winslow et al. | 2005/0015095 A1 | 1/2005 | Keller |
| 7,780,670 B2 | 8/2010 | Bonutti | 2005/0015149 A1 | 1/2005 | Michelson |
| 7,789,914 B2 | 9/2010 | Michelson | 2005/0033428 A1 | 2/2005 | Keller |
| 7,794,502 B2 | 9/2010 | Michelson | 2005/0033435 A1 | 2/2005 | Belliard et al. |
| 7,799,053 B2 | 9/2010 | Haid, Jr. et al. | 2005/0038512 A1 | 2/2005 | Michelson |
| 7,799,057 B2 | 9/2010 | Hudgins et al. | 2005/0038516 A1 | 2/2005 | Spoonamore |
| 7,799,081 B2 | 9/2010 | McKinley | 2005/0049590 A1 | 3/2005 | Alleyne et al. |
| 7,811,326 B2 | 10/2010 | Braddock, Jr. et al. | 2005/0060037 A1 | 3/2005 | Michelson |
| 7,819,903 B2 | 10/2010 | Fraser et al. | 2005/0065608 A1 | 3/2005 | Michelson |
| 7,824,445 B2 | 11/2010 | Biro et al. | 2005/0131542 A1 | 6/2005 | Benzel et al. |
| 7,833,255 B2 | 11/2010 | Chow et al. | 2005/0131544 A1 | 6/2005 | Kuras et al. |
| 7,842,088 B2 | 11/2010 | Rashbaum et al. | 2005/0143733 A1 | 6/2005 | Petit |
| 7,846,207 B2 | 12/2010 | Lechmann et al. | 2005/0143825 A1 | 6/2005 | Enayati |
| 7,850,731 B2 | 12/2010 | Brittan et al. | 2005/0154462 A1 | 7/2005 | Zucherman et al. |
| 7,850,732 B2 | 12/2010 | Heinz | 2005/0273171 A1 | 12/2005 | Gordon et al. |
| 7,850,733 B2 | 12/2010 | Baynham et al. | 2005/0273173 A1 | 12/2005 | Gordon et al. |
| 7,862,616 B2 | 1/2011 | Lechmann et al. | 2005/0273174 A1 | 12/2005 | Gordon et al. |
| 7,871,441 B2 | 1/2011 | Eckman | 2005/0273175 A1 | 12/2005 | Gordon et al. |
| 7,875,076 B2 | 1/2011 | Mathieu et al. | 2005/0278026 A1 | 12/2005 | Gordon et al. |
| 7,887,591 B2 | 2/2011 | Aebi et al. | 2005/0283244 A1 | 12/2005 | Gordon et al. |
| 7,892,261 B2 | 2/2011 | Bonutti | 2005/0283245 A1 | 12/2005 | Gordon et al. |
| 7,892,286 B2 | 2/2011 | Michelson | 2005/0283247 A1 | 12/2005 | Gordon et al. |
| 7,896,919 B2 | 3/2011 | Belliard et al. | 2005/0283248 A1 | 12/2005 | Gordon et al. |
| 7,909,871 B2 | 3/2011 | Abdou | 2006/0016768 A1 | 1/2006 | Grichar et al. |
| 7,914,560 B2 | 3/2011 | Hoy et al. | 2006/0036261 A1 | 2/2006 | McDonnell |
| 7,922,729 B2 | 4/2011 | Michelson | 2006/0036325 A1 | 2/2006 | Paul et al. |
| 7,931,674 B2 | 4/2011 | Zucherman et al. | 2006/0058878 A1 | 3/2006 | Michelson |
| 7,931,840 B2 | 4/2011 | Michelson | 2006/0085076 A1 | 4/2006 | Krishna et al. |
| 7,935,149 B2 | 5/2011 | Michelson | 2006/0085077 A1 | 4/2006 | Cook et al. |
| 7,951,198 B2 | 5/2011 | Sucec et al. | 2006/0089717 A1 | 4/2006 | Krishna et al. |
| 7,955,390 B2 | 6/2011 | Fallin et al. | 2006/0095136 A1 | 5/2006 | McLuen |
| 7,972,337 B2 | 7/2011 | Boyajian et al. | 2006/0129244 A1 | 6/2006 | Ensign |
| 7,972,363 B2 | 7/2011 | Moskowitz et al. | 2006/0149273 A1 | 7/2006 | Ross et al. |
| 7,972,365 B2 | 7/2011 | Michelson | 2006/0178745 A1 | 8/2006 | Bartish et al. |
| 7,976,566 B2 | 7/2011 | Michelson | 2006/0206208 A1 | 9/2006 | Michelson |
| 7,985,255 B2 | 7/2011 | Bray et al. | 2006/0241764 A1 | 10/2006 | Michelson |
| 7,985,258 B2 | 7/2011 | Zdeblick et al. | 2006/0253201 A1 | 11/2006 | McLuen |
| 7,993,373 B2 | 8/2011 | Hoy et al. | 2006/0259147 A1 | 11/2006 | Krishna et al. |
| 7,998,177 B2 | 8/2011 | Hoy et al. | 2007/0010886 A1 | 1/2007 | Banick et al. |
| 7,998,178 B2 | 8/2011 | Hoy et al. | 2007/0016297 A1 | 1/2007 | Johnson |
| 7,998,211 B2 | 8/2011 | Baccelli et al. | 2007/0032871 A1 | 2/2007 | Michelson |
| 8,002,835 B2 | 8/2011 | Zeegers | 2007/0118223 A1 | 5/2007 | Allard et al. |
| 8,007,534 B2 | 8/2011 | Michelson | 2007/0123985 A1 | 5/2007 | Errico et al. |
| 8,021,401 B2 | 9/2011 | Carl et al. | 2007/0179623 A1 | 8/2007 | Trieu et al. |
| 8,021,430 B2 | 9/2011 | Michelson | 2007/0250167 A1 | 10/2007 | Bray et al. |
| 8,043,334 B2 | 10/2011 | Fisher et al. | 2007/0250168 A1 | 10/2007 | Lechmann et al. |
| 8,062,336 B2 | 11/2011 | Triplett et al. | 2007/0260249 A1 | 11/2007 | Boyajian et al. |
| 8,062,375 B2 | 11/2011 | Glerum et al. | 2007/0270954 A1 | 11/2007 | Wu |
| 8,066,741 B2 | 11/2011 | Fallin et al. | 2007/0270961 A1 | 11/2007 | Ferguson |

| | | |
|---|---|---|
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0299524 A1 | 12/2007 | Rivin |
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0161930 A1 | 7/2008 | Carls et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0053693 A1 | 3/2012 | Zeegers |

FOREIGN PATENT DOCUMENTS

| | | |
|---|---|---|
| CA | 2472708 | 2/2005 |
| CA | 2533473 | 3/2011 |
| DE | 4328690 | 3/1995 |
| DE | 29911422 | 8/1999 |
| DE | 20320454 | 10/2004 |
| DE | 10323363 | 12/2004 |
| EP | 0637439 | 2/1995 |
| EP | 0697200 | 2/1996 |
| EP | 0951879 | 10/1999 |
| EP | 1222903 | 7/2002 |
| EP | 1287795 | 3/2003 |
| EP | 1504733 | 2/2005 |
| FR | 2879436 | 6/2006 |
| FR | 2880795 | 7/2006 |
| FR | 2887762 | 1/2007 |
| FR | 2891135 | 3/2007 |
| FR | 2893838 | 6/2007 |
| FR | 2916956 | 12/2008 |
| WO | WO9515133 | 6/1995 |
| WO | WO9817209 | 4/1998 |
| WO | WO9956676 | 11/1999 |
| WO | WO0143620 | 6/2001 |
| WO | WO0213732 | 2/2002 |
| WO | WO02058599 | 8/2002 |
| WO | WO03005939 | 1/2003 |
| WO | WO03026522 | 4/2003 |
| WO | WO2004034935 | 4/2004 |
| WO | WO2004039291 | 5/2004 |
| WO | WO2004071360 | 8/2004 |
| WO | WO2004089256 | 10/2004 |
| WO | WO2005007040 | 1/2005 |
| WO | WO2005007044 | 1/2005 |
| WO | WO2005051243 | 6/2005 |
| WO | WO2006016384 | 2/2006 |
| WO | WO2006047587 | 5/2006 |
| WO | WO2006062960 | 6/2006 |
| WO | WO2006120505 | 11/2006 |
| WO | WO2006130460 | 12/2006 |
| WO | WO2007000654 | 1/2007 |
| WO | WO2007034310 | 3/2007 |
| WO | WO2007063398 | 6/2007 |
| WO | WO2007078978 | 7/2007 |

| | | |
|---|---|---|
| WO | WO2008099277 | 8/2008 |
| WO | WO2008149223 | 12/2008 |
| WO | WO2009033100 | 3/2009 |
| WO | WO2011080535 | 7/2011 |

OTHER PUBLICATIONS

U.S. Patent & Trademark Office; Notice of Allowance in Application Serial No. 10476565; Nov. 29, 2007; USPTO; Alexandria, VA; All Pages.
LDR Medical, by its attorneys; Amendment After Final in Application Serial No. 10476565; Nov. 29, 2007; USPTO; Alexandria, VA; All Pages.
LDR Medical, by its attorneys; Reply to Office Action in Application Serial No. 10476565; Nov. 6, 2007; USPTO; Alexandria, VA; All Pages.
U.S. Patent and Trademark Office; Office Action in Application Serial No. 10476565; May 7, 2007; USPTO; Alexandria, VA; All Pages.
LDR Medical, by its attorneys; Reply to Office Action in Application Serial No. 10476565; Jan. 18, 2007; USPTO; Alexandria, VA; All Pages.
U.S. Patent & Trandmark Office; Office Action in Application Serial No. 10476565; Jul. 18, 2006; USPTO; Alexandria, VA; All Pages.
LDR Medical, by its attorneys; Reply to Office Action in Application Serial No. 12025677; Dec. 20, 2013; USPTO; Alexandria, VA; All Pages.
U.S. Patent & Trademark Office; Office Action in Application Serial No. 12025677; Jun. 20, 2013; USPTO; Alexandria, VA; All Pages.
LDR Medical, by its attorneys; Reply to Office Action in Application Serial No. 12025677; Dec. 29, 2012; USPTO; Alexandria VA; All Pages.
U.S. Patent & Trademark Office; Office Action in Application Serial No. 12025677; Jun. 29, 2012; USPTO; Alexandria, VA; All Pages.
LDR Medical, by its attorneys; Reply to Office Action in Application Serial No. 12025677; Apr. 9, 2012; USPTO; Alexandria, VA; All Pages.
U.S. Patent & Trademark Office; Office Action in Application Serial No. 12025677; Oct. 7, 2011; USPTO; Alexandria, VA; All Pages.
U.S. Patent & Trademark Office; Notice of Allowance in Application Serial No. 10494418; Sep. 20, 2005; USPTO; Alexandria, VA; All Pages.
U.S. Patent & Trademark Office; Notice of Allowance in Application Serial No. 10533846; Nov. 4, 2009; USPTO; Alexandria, VA; All Pages.
U.S. Patent & Trademark Office; Notice of Allowance in Application Serial No. 12424364; Aug. 2, 2012; USPTO; Alexandria, VA; All Pages.
U.S. Patent & Trademark Office; Notice of Allowance in Application Serial No. 12424364; Jul. 24, 2012; USPTO; Alexandria, VA; All Pages.
LDR Medical, by its attorneys; Reply to Office Action in Application Serial No. 12424364; Jul. 6, 2012; USPTO; Alexandria, VA; All Pages.
U.S. Patent & Trademark Office; Office Action in Application Serial No. 12424364; May 23, 2012; USPTO; Alexandria VA; All Pages.
LDR Medical, by its attorneys; Interview Summary and Terminal Disclaimer in Application Serial No. 12424364; May 22, 2012; USPTO; Alexandria, VA; All Pages.
LDR Medical, by its attorneys; Reply to Office Action in Application Serial No. 12424364; Feb. 27, 2012; USPTO; All Pages.
U.S. Patent & Trademark Office; Office Action in Application Serial No. 12424364; Jan. 26, 2012; USPTO; Alexandria, VA; All Pages.
LDR Medical, by its attorneys; Reply to Office Action in Application Serial No. 12424364; Nov. 18, 2011; USPTO; Alexandria, VA; All Pages.
U.S. Patent & Trademark Office; Office Action in Application Serial No. 12424364; May 18, 2011; USPTO; Alexandria, VA; All Pages.
U.S. Patent & Trademark Office; Office Action in Application Serial No. 13616448; Aug. 22, 2013; USPTO; Alexandria, VA; All Pages.
LDR Medical, by its attorneys; Request for Continued Examination in Application Serial No. 11051710; Jul. 11, 2013; USPTO; Alexandria, VA; All Pages.

U.S. Patent & Trademark Office; Notice of Allowance in Application Serial No. 11051710; Apr. 11, 2013; USPTO; Alexandria, VA; All Pages.
LDR Medical, by its attorneys; Appeal Brief in Application Serial No. 11051710; Jan. 15, 2013; USPTO; Alexandria VA; All Pages.
U.S. Patent & Trademark Office; Office Action in Application Serial No. 11051710; Dec. 15, 2011; USPTO; Alexandria, VA; All Pages.
LDR Medical, by its attorneys; Reply to Office Action in Application Serial No. 11051710; Oct. 11, 2011; USPTO; Alexandria, VA; All Pages.
U.S. Patent & Trademark Office; Office Action in Application Serial No. 11051710; Apr. 11, 2011; USPTO; Alexandria, VA; All Pages.
Ldr Medical, by its attorneys; Reply to Office Action in Application Serial No. 11051710; Jan. 20, 2011; USPTO; Alexandria, VA; All Pages.
U.S. Patent & Trademark Office; Office Action in Application Serial No. 11051710; Jul. 20, 2010; USPTO; Alexandria, VA; All Pages.
LDR Medical, by its attorneys; Reply to Office Action in Application Serial No. 11051710; Apr. 26, 2010; USPTO; Alexandra, VA; All Pages.
U.S. Patent & Trademark Office; Office Action in Application Serial No. 11051710; Oct. 26, 2009; USPTO; Alexandria, VA; All Pages.
U.S. Patent & Trademark Office; Notice of Allowance in Application Serial No. 11098266; Apr. 21, 2008; USPTO; Alexandria, VA; All Pages.
LDR Medical, by its attorneys; Reply to Office Action in Application Serial No. 11098266; Feb. 6, 2008; USPTO; Alexandria, VA; All Pages.
U.S. Patent & Trademark Office; Office Action in Application Serial No. 11098266; Aug. 6, 2007; USPTO; Alexandria, VA; All Pages.
LDR Medical, by its attorneys; Reply to Office Action in Application Serial No. 11098266; May 23, 2007; USPTO; Alexandria, VA; All Pages.
U.S. Patent & Trademark Office; Office Action in Application Serial No. 11098266; Nov. 29, 2006; USPTO; Alexandria, VA; All Pages.
LDR Medical, by its attorneys; Reply to Office Action in Application Serial No. 11098266; Aug. 22, 2006; USPTO; Alexandria, VA; All Pages.
U.S. Patent & Trademark Office; Office Action in Application Serial No. 11098266; Mar. 22, 2006; USPTO; Alexandria, VA; All Pages.
U.S. Patent & Trademark Office; Notice of Allowance in Application Serial No. 12391086; Apr. 15, 2011; USPTO; Alexandria, VA; All Pages.
LDR Medical, by its attorneys; Reply to Office Action in Application Serial No. 12391086; Jan. 31, 2011; USPTO; Alexandria, VA; All Pages.
U.S. Patent & Trademark Office; Office Action in Application Serial No. 12391086; Jul. 29, 2010; USPTO; Alexandria, VA; All Pages.
U.S. Patent & Trademark Office; Office Action in Application Serial No. 13215123; Nov. 18, 2013; USPTO; Alexandria, VA; All Pages.
LDR Medical, by its attorneys; Reply to Office Action in Application Serial No. 13215123; Nov. 11, 2013; USPTO; Alexandria, VA; All Pages.
LDR Medical, by its attorneys; Reply to Office Action in Application U.S. Serial 13215123; Oct. 24, 2013; USPTO; Alexandria, VA; All Pages.
U.S. Patent & Trademark Office; Office Action in Application Serial No. 13215123; May 24, 2013; USPTO; Alexandria, VA; All Pages.
LDR Medical, by its attorneys; Reply to Office Action in Application Serial No. 13215123; Mar. 20, 2013; USPTO; Alexandria, VA; All Pages.
LDR Medical, by its attorneys; Terminal Disclaimer in Application Serial No. 13215123; Mar. 20, 2013; USPTO; Alexandria, VA; All Pages.
U.S. Patent & Trademark Office; Office Action in Application Serial No. 13215123; Nov. 20, 2012; USPTO; Alexandria, VA; All Pages.
U.S. Patent & Trademark Office; Notice of Allowance in Application Serial No. 11109276; Dec. 8, 2009; USPTO; Alexandria, VA; All Pages.
U.S. Patent & Trademark Office; Notice of Allowance in Application Serial No. 12360050; Aug. 2, 2012; USPTO; Alexandria, VA; All Pages.

U.S. Patent & Trademark Office; Notice of Allowance in Application Serial No. 12360050; Jul. 6, 2012; USPTO; Alexandria, VA; All Pages.
U.S. Patent & Trademark Office; Notice of Allowance in Application Serial No. 12360050; May 18, 2012; USPTO; Alexandria, VA; All Pages.
U.S. Patent & Trademark Office; Notice of Allowance in Application Serial No. 12360050; Mar. 26, 2012; USPTO; Alexandria, VA; All Pages.
LDR Medical, by its attorneys; Reply to Office Action in Application Serial No. 12360050; Mar. 6, 2012; USPTO; Alexandria, VA; All Pages.
U.S. Patent & Trademark Office; Office Action in Application Serial No. 12360050; Sep. 6, 2011; USPTO; Alexandria, VA; All Pages.
LDR Medical, by its attorneys; Reply to Office Action in Application Serial No. 12360050; Jun. 16, 2011; USPTO; Alexandria, VA; All Pages.
U.S. Patent & Trademark Office; Office Action in Application Serial No. 12360050; Dec. 17, 2010; USPTO; Alexandria, VA; All Pages.
U.S. Patent & Trademark Office; Office Action in Application Serial No. 13603043; Nov. 21, 2013; USPTO; Alexandria, VA; All Pages.
LDR Medical, by its attorneys; Reply to Office Action in Application Serial No. 13603043; Oct. 9, 2013; USPTO; Alexandria, VA; All Pages.
U.S. Patent & Trademark Office; Office Action in Application Serial No. 13603043; Apr. 9, 2013; USPTO; Alexandria, VA; All Pages.
U.S. Patent & Trademark Office; Notice of Allowance in Application Serial No. 11341007; Jul. 26, 2010; USPTO; Alexandria, VA; All Pages.
LDR Medical, by its attorneys; Reply to Office Action in Application Serial No. 11341007; Jun. 17, 2010; USPTO; Alexandria, VA; All Pages.
U.S. Patent & Trademark Office; Office Action in Application Serial No. 11341007; Dec. 17, 2009; USPTO; Alexandria, VA; All Pages.
LDR Medical, by its attorneys; Reply to Office Action in Application Serial No. 11341007; Oct. 13, 2009; USPTO; Alexandria, VA; All Pages.
LDR Medical, by its attorneys; Reply to Office Action in Application Serial No. 12955898; Jul. 10, 2013; USPTO; Alexandria, VA; All Pages.
U.S. Patent and Trademark Office; Office Action in Application Serial No. 12955898; Jan. 10, 2013; USPTO; Alexandria, VA; All Pages.
LDR Medical, by its attorneys; Reply to Office Action in Application Serial No. 12955898; Dec. 3, 2012; USPTO; Alexandria, VA; All Pages.
U.S. Patent & Trademark Office; Office Action in Application Serial No. 12955898; Jun. 1, 2012; USPTO; Alexandria, VA; All Pages.
LDR Medical, by its attorneys; Reply to Office Action in Application Serial No. 12955898; Apr. 19, 2012; USPTO; Alexandria, VA; All Pages.
U.S. Patent & Trademark Office; Office Action in Application Serial No. 12955898; Mar. 19, 2012; USPTO; Alexandria, VA; All Pages.
LDR Medical, by it attorneys; Reply Brief in Application Serial No. 11362253; Aug. 20, 2012; USPTO; Alexandria, VA; All Pages.
U.S. Patent & Trademark Office; Examiners Answer to Appeal Brief in Application Serial No. 11362253; Jun. 20, 2012; USPTO; Alexandria, VA; All Pages.
LDR Medical, by its attorneys; Appeal Brief in Application Serial No. 11362253; Apr. 9, 2012; USPTO; Alexandria, VA; All Pages.
U.S. Patent & Trademark Office; Office Action in Application Serial No. 11362253; Mar. 8, 2011; USPTO; Alexandria, VA; All Pages.
LDR Medical, by its attorneys; Reply to Office Action in Application Serial No. 11362253; Dec. 20, 2010; USPTO; Alexandria, VA; All Pages.
U.S. Patent & Trademark Office; Office Action in Application Serial No. 11362253; Jun. 18, 2010; USPTO; Alexandria, VA; All Pages.
LDR Medical, by its attorneys; Reply to Office Action in Application Serial No. 11362253; Apr. 15, 2010; USPTO; Alexandria, VA; All Pages.
U.S. Patent & Trademark Office; Office Action in Application Serial No. 11362253; Oct. 15, 2009; USPTO; Alexandria, VA; All Pages.
LDR Medical, by its attorneys; Reply to Office Action in Application Serial No. 11362253; Aug. 18, 2009; USPTO; Alexandria, VA; All Pages.
U.S. Patent & Trademark Office; Office Action in Application Serial No. 11362253; Feb. 18, 2009; USPTO; Alexandria, VA; All Pages.
LDR Medical, by its attorneys; Reply to Office Action in Application Serial No. 13620797; Nov. 5, 2013; USPTO; Alexandria, VA; All Pages.
U.S. Patent & Trademark Office; Office Action in Application Serial No. 13620797; Jul. 5, 2013; USPTO; Alexandria, VA; All Pages.
U.S. Patent & Trademark Office; Notice of Allowance in Application Serial No. 12134884; Nov. 1, 2012; USPTO; Alexandria, VA; All Pages.
LDR Medical, by its attorneys; Reply to Office Action in Application Serial No. 12134884; Jul. 31, 2012; USPTO; Alexandria, VA; All Pages.
U.S. Patent & Trademark Office; Office Action in Application Serial No. 12134884; Jan. 31, 2012; USPTO; Alexandria, VA; All Pages.
U.S. Patent & Trademark Office; Notice of Allowance in Application Serial No. 11676237; Feb. 20, 2013; USPTO; Alexandria, VA; All Pages.
LDR Medical, by its attorneys; Reply to Office Action in Application Serial No. 11676237; Feb. 6, 2013; USPTO; Alexandria, VA; All Pages.
U.S. Patent & Trademark Office; Office Action in Application Serial No. 11676237; Nov. 6, 2012; USPTO;Alexandria, VA; All Pages.
LDR Medical, by its attorneys; Reply to Office Action in Application Serial No. 11676237; Jul. 16, 2012; USPTO; Alexandria, VA; All Pages.
U.S. Patent & Trademark Office; Office Action in Application U.S. Serial 11676237; Feb. 16, 2012; USPTO; Alexandria, VA; All Pages.
LDR Medical, by its attorneys; Appeal Brief in Application U.S. Serial 11676237; Oct. 17, 2011; USPTO; Alexandria, VA; All Pages.
U.S. Patent & Trademark Office; Office Action in Application Serial No. 11676237; Sep. 15, 2010; USPTO; Alexandria, VA; All Pages.
LDR Medical, by its attorneys; Reply to Office Action in Application Serial No. 11676237; Jun. 18, 2010; USPTO; Alexandria, VA; All Pages.
U.S. Patent & Trademark Office; Office Action in Application Serial No. 11676237; Dec. 18, 2009; USPTO; Alexandria, VA; All Pages.
LDR Medical, by its attorneys; Reply to Office Action in Application Serial No. 11676237; Sep. 21, 2009; USPTO; Alexandria, VA; All Pages.
U.S. Patent & Trademark Office; Office Action in Application Serial No. 13919704; Nov. 18, 2013; USPTO; Alexandria, VA; All Pages.
U.S. Patent & Trademark Office; Notice of Allowance in Application Serial No. 12527373; Dec. 24, 2013; USPTO; Alexandria, VA; All Pages.
LDR Medical, by its attorneys; Request for Continued Examination in Application Serial No. 12527373; Dec. 2, 2013; USPTO; Alexandria, VA; All Pages.
U.S. Patent & Trademark Office; Notice of Allowance in Application Serial No. 12527373; Aug. 30, 2013; USPTO; Alexandria, VA; All Pages.
U.S. Patent & Trademark Office; Interview Summary in Application Serial No. 12527373; Aug. 30, 2013; USPTO; Alexandria, VA; All Pages.
LDR Medical, by its attorneys; Appeal Brief in Application Serial No. 12527373; Apr. 24, 2013; USPTO; Alexandria, VA; All Pages.
U.S. Patent & Trademark Office; Office Action in Application Serial No. 12527373; Sep. 24, 2012; USPTO; Alexandria, VA; All Pages.
LDR Medical, by its attorneys; Reply to Office Action in Application Serial No. 12527373; Jun. 21, 2012; USPTO; Alexandria, VA; All Pages.
U.S. Patent & Trademark Office; Office Action in Application Serial No. 12527373; Dec. 21, 2011; USPTO; Alexandria, VA; All Pages.
LDR Medical, by its attorneys; Reply to Office Action in Application Serial No. 13158761; Nov. 14, 2013; USPTO; Alexandria, VA; All Pages.
U.S. Patent & Trademark Office; Office Action in Application Serial No. 13158761; Aug. 14, 2013; USPTO; Alexandria, VA; All Pages.

U.S. Patent & Trademark Office; Interview Summary in Application Serial No. 13158761; Aug. 1, 2013; USPTO; Alexandria, VA; All Pages.
LDR Medical, by its attorneys; Reply to Office Action in Application Serial No. 13158761; Jul. 29, 2013; USPTO; Alexandria, VA; All Pages.
U.S. Patent & Trademark Office; Office Action in Application Serial No. 13158761; Feb. 28, 2013; USPTO; Alexandria, VA; All Pages.
LDR Medical, by its attorneys; Reply to Office Action in Application Serial No. 13158761; Nov. 19, 2012; USPTO; Alexandria, VA; All Pages.
U.S. Patent & Trademark Office; Interview Summary in Application Serial No. 13158761; Oct. 31, 2012; USPTO; Alexandria, VA; All Pages.
U.S. Patent & Trademark Office; Office Action in Application Serial No. 13158761; Oct. 17, 2012; USPTO; Alexandria, VA; All Pages.
National Institute of Industrial Property (France); Preliminary Search Report in Fench Pub. No. FR2879436; Aug. 11, 2005; National Institute of Industrial Property (France); France; all pages.
National Institute of Industrial Property (France); Preliminary Search Report in Fench Pub. No. FR2887762; Dec. 21, 2005; National Institute of Industrial Property (France); France; all pages.
National Institute of Industrial Property (France); Preliminary Search Report in Fench Pub. No. FR2891135; Jun. 27, 2006; National Institute of Industrial Property (France); France; all pages.
National Institute of Industrial Property (France); Preliminary Search Report in Fench Pub. No. FR2893838; Aug. 4, 2006; National Institute of Industrial Property (France); France; all pages.
National Institute of Industrial Property (France); Preliminary Search Report in Fench Pub. No. FR2916956; Jan. 30, 2008; National Institute of Industrial Property (France); France; all pages.
National Institute of Industrial Property (France); Preliminary Search Report in Fench Pub. No. FR2987256; Dec. 5, 2012; National Institute of Industrial Property (France); France; all pages.
World Intellectual Property Organization; International Preliminary Report on Patentability for PCT Pub'n No. WO2005074839; Jan. 16, 2006; WIPO; Geneva, Switzerland; all pages.
World Intellectual Property Organization; International Preliminary Report on Patentability for PCT Pub'n No. WO2005104996; Jun. 28, 2006; WIPO; Geneva, Switzerland; all pages.
World Intellectual Property Organization; International Preliminary Report on Patentability for PCT Pub'n No. WO2006120505; Feb. 22, 2007; WIPO; Geneva, Switzerland; all pages.
World Intellectual Property Organization; International Preliminary Report on Patentability for PCT Pub'n No. WO2007000654; Jul. 19, 2007; WIPO; Geneva, Switzerland; all pages.
World Intellectual Property Organization; International Preliminary Report on Patentability for PCT Pub'n No. WO2007034310; Aug. 14, 2007; WIPO; Geneva, Switzerland; all pages.
World Intellectual Property Organization; International Preliminary Report on Patentability for PCT Pub'n No. WO2007063398; Nov. 12, 2007; WIPO; Geneva, Switzerland; all pages.
World Intellectual Property Organization; International Preliminary Report on Patentability for PCT Pub'n No. WO2008149223; Aug. 5, 2009; WIPO; Geneva, Switzerland; all pages.
World Intellectual Property Organization; International Search Report for PCT Pub'n No. WO2006120505; Aug. 21, 2006; WIPO; Geneva, Switzerland; all pages.
World Intellectual Property Organization; International Search Report for PCT Pub'n No. WO2007000654; Mar. 14, 2007; WIPO; Geneva, Switzerland; all pages.
World Intellectual Property Organization; International Search Report for PCT Pub'n No. WO2007034310; Feb. 13, 2007; WIPO; Geneva, Switzerland; all pages.
World Intellectual Property Organization; International Search Report for PCT Pub'n No. WO2007063398; Jul. 13, 2007; WIPO; Geneva, Switzerland; all pages.
World Intellectual Property Organization; International Search Report for PCT Pub'n No. WO2008149223; Oct. 31, 2008; WIPO; Geneva, Switzerland; all pages.
World Intellectual Property Organization; International Search Report for PCT Pub'n No. WO2011080535; Jan. 24, 2011; WIPO; Geneva, Switzerland; all pages.
World Intellectual Property Organization; International Search Report for PCT Pub'n No. WO2013124453; May 29, 2013; WIPO; Geneva, Switzerland; all pages.
World Intellectual Property Organization; International Search Report for PCT Pub'n No. WO2008099277; Nov. 7, 2008; WIPO; Geneva, Switzerland; all pages.
World Intellectual Property Organization; Written Opinon of the International Searching Authority for PCT Pub'n No. WO2005074839; Jun. 24, 2005; WIPO; Geneva, Switzerland; all pages.
World Intellectual Property Organization; Written Opinon of the International Searching Authority for PCT Pub'n No. WO2005104996; Sep. 12, 2005; WIPO; Geneva, Switzerland; all pages.
World Intellectual Property Organization; Written Opinon of the International Searching Authority for PCT Pub'n No. WO2006120505; Aug. 21, 2006; WIPO; Geneva, Switzerland; all pages.
World Intellectual Property Organization; Written Opinon of the International Searching Authority for PCT Pub'n No. WO2007000654; Mar. 14, 2007; WIPO; Geneva, Switzerland; all pages.
World Intellectual Property Organization; Written Opinon of the International Searching Authority for PCT Pub'n No. WO2007034310; Feb. 13, 2007; WIPO; Geneva, Switzerland; all pages.
World Intellectual Property Organization; Written Opinon of the International Searching Authority for PCT Pub'n No. WO2007063398; Jul. 13, 2007; WIPO; Geneva, Switzerland; all pages.
World Intellectual Property Organization; Written Opinon of the International Searching Authority for PCT Pub'n No. WO2008149223; Oct. 31, 2008; WIPO; Geneva, Switzerland; all pages.
World Intellectual Property Organization; Written Opinon of the International Searching Authority for PCT Pub'n No. WO2008099277; Nov. 7, 2008; WIPO; Geneva, Switzerland; all pages.

* cited by examiner

*Primary Examiner* — Sameh Boles (74) *Attorney, Agent, or Firm* — Denko Coburn Lauff LLP (57) ABSTRACT

The present invention relates to an intervertebral disc prosthesis and insertion instrumentation, the prosthesis comprising at least first and second osseous anchoring means, the first osseous anchoring means disposed proximal to the periphery of the plate on which it is situated and the second osseous anchoring means being offset along the antero-posterior axis, the second osseous anchoring means comprising a basal portion and a sharp-edged portion of width narrower than the basal portion. The instrumentation comprises a rod fitted with at least two feet forming a clip and sliding in a tube, sliding the rod in the tube, in the direction of the manipulation end, causing closing of the clip by contact between the exterior of the feet and a truncated portion of the tube and sliding the rod in the tube, in the direction of the prehension end, causing opening of the clip by contact between an axis and the interior of the feet of the rod.

8 Claims, 6 Drawing Sheets

INTERVERTEBRAL DISC PROSTHESIS AND INSTRUMENTATION FOR INSERTION OF THE PROSTHESIS BETWEEN THE VERTEBRAE

CROSS REFERENCE TO RELATED APPLICATIONS

This application is a divisional of U.S. patent application Ser. No. 11/362,253 filed Feb. 24, 2006, which claims priority under 35 U.S.C. 119 to French Patent Application No. 05 12133, filed in FRANCE on Nov. 30, 2005.

BACKGROUND OF THE INVENTION

The present invention concerns an intervertebral disc prosthesis, intended to be substituted for fibro-cartilaginous discs ensuring connection between the vertebrae of the spinal column.

Various types of intervertebral disc prostheses are known in the prior art. Numerous prostheses, such as for example in the patent applications WO 02 089 701 and WO 2004/041129, are constituted by a lower plate and an upper plate forming a sort of cage articulated about a central core. Other prostheses such as those described in the U.S. Pat. No. 5,676,701 and in the patent application WO 03/059212 A1, for example, comprise only a lower plate and an upper plate articulated to one another by means of an articulation surface. The advantage of these two types of articulated prostheses is that they offer freedom of movement for the patient wearing the prosthesis, by enabling inclination and/or rotation of one of the plates relative to the other. The additional advantage of prostheses comprising a central core, mobile between the plates, is that they allow spontaneous positioning of the core in the ideal position to absorb the constraints imposed on the prosthesis. Some of the prostheses whereof the central core is mobile between the plates comprise cooperation means present on the core and on at least one of the plates to limit displacement of the core. In these prostheses described in the prior art, osseous anchoring means are likewise known which fix each of the plates of the prosthesis in each of the vertebrae between which the prosthesis is intended to be implanted. These osseous anchoring means can consist of fins intended to be fixed on the plates of the prosthesis and cooperate with a groove made in the surface of the vertebral plates or in anchors intended to be planted in the vertebral body.

However, the disadvantage of these prostheses is that they are not easy to insert between the vertebrae, since implantation requires good stability of the different elements of the prosthesis between one another. This stability is often missing in prostheses known from the prior art and the known instrumentation does not generally ensure stability of the elements of the prosthesis. In fact, the articulated plates of the prostheses possess degrees of liberty conferring comfort to the patient, but discomfort for the surgeon who fits them. The plates risk inclining and turning about their articulation surfaces. The surgeon is therefore not guaranteed that the elements are properly aligned in the antero-posterior axis of the vertebral column.

SUMMARY

In this context, it is interesting to propose a prosthesis and associated instrumentation enabling the prosthesis to be implanted between the vertebrae, while retaining the necessary alignment of the different elements of the prosthesis between one another. The aim of the present invention therefore is to eliminate certain disadvantages of the prior art by proposing an intervertebral disc prosthesis and instrumentation for insertion of the prosthesis between the vertebrae allowing the prosthesis to be implanted by following a defined axis.

This aim is attained by an intervertebral disc prosthesis comprising at least two plates, so-called first and second plates, articulated between one another by means of a curved surface, so-called articulation, of at least one of the plates, allowing pivoting and/or inclination of the plates relative to one another, by rotation about, respectively, an axis substantially perpendicular to the plane of the plates and an axis substantially in the plane of the plates, each of the plates comprising a so-called contact surface, intended to be made solid with a vertebral plate of one of the vertebrae between which the prosthesis is intended to be implanted, characterised in that the contact surface of at least one of the plates comprises at least first osseous anchoring means and at least second osseous anchoring means, the first osseous anchoring means extending to in the vicinity of the periphery of the plate on which it is situated and the second osseous anchoring means being offset according to the antero-posterior axis relative to the first osseous anchoring means, said second osseous anchoring means offset comprising a portion, so-called basal, solid with the plate on which it is situated and a portion, so-called sharp-edged, of width narrower than the basal portion and forming a guide blade intended to prevent rotation of the plates of the prosthesis between one another and facilitate insertion of the prosthesis.

In accordance with another specific characteristic, the second plate comprises a curved articulation surface whereof at least one part cooperates with a curved articulation surface of the first plate to which it is complementary, to allow pivoting and/or inclination of the plates relative to one another.

In accordance with another specific characteristic, the curved surface of the first plate is concave and the curved articulation surface of the second plate is convex.

In accordance with another specific characteristic, the curved surface of the first plate is convex and the curved articulation surface of the second plate is concave.

In accordance with another specific characteristic, it likewise comprises a core comprising a plane surface and a curved articulation surface and in that only the first plate comprises a curved articulation surface cooperating with at least one part of the curved surface of the core to which it is complementary, to allow pivoting and/or inclination of the plates relative to one another, the plane surface of the core cooperating with at least one part of a plane surface of the second plate to allow translation and/or rotation of the core relative to the second plate in at least one direction perpendicular to the vertical axis of the backbone, the second plate comprising cooperation means complementary to cooperation means of the core allowing at least this translation of the core to be limited or eliminated relative to the second plate.

In accordance with another specific characteristic, the curved surface of the first plate is concave and the curved surface of the core is convex.

In accordance with another specific characteristic, the curved surface of the first plate is convex and the curved surface of the core is concave.

In accordance with another specific characteristic, the first osseous anchoring means of the plates consist of at least one winglet located in the vicinity of the periphery of the plate and fitted with notches oriented so as to oppose withdrawal of the prosthesis from the discal space.

In accordance with another specific characteristic, the notches of the first osseous anchoring means are at a height increasing in the postero-anterior direction, such that the notches are at a height greater at the front than at the rear of the prosthesis and so that the insertion of the prosthesis in the discal space, in the antero-posterior direction of the vertebrae is facilitated by the notches attacking the osseous tissue not yet attacked by the preceding notches.

In accordance with another specific characteristic, at least the anterior edge of at least one of the plates of the prosthesis comprises 3 support faces whereof one leading face substantially perpendicular to the insertion axis of the prosthesis in the discal space and two antero-lateral faces each forming, in the plane of the plate, an angle with the anterior face and with one of the lateral edges of the plate, these 3 support faces allowing stabilising of the prosthesis during its insertion in the discal space by an instrument whereof at least a portion has a shape complementary to these 3 support faces.

In accordance with another specific characteristic, at least one of the plates has, at least on its posterior edge, at least one chamfer facilitating insertion of the prosthesis in the discal space.

In accordance with another specific characteristic, the second osseous anchoring means of the plates consists of at least one aileron located in the vicinity of an edge of the plate and oriented in the insertion axis of the prosthesis between the vertebrae.

In accordance with another specific characteristic, the aileron has a lesser height at its posterior end than at its anterior end, this difference in height imparting to the aileron an inclined profile facilitating its insertion in the discal space in the antero-posterior direction.

In accordance with another specific characteristic, at least one of the plates comprises at least one default form, such as a notch, allowing the fitting of the end of a prehension device to the prosthesis.

In accordance with another specific characteristic, the cooperation means of the second plate are male means located in the vicinity of the edges of the second plate and cooperating with female means of the core.

In accordance with another specific characteristic, the male cooperation means of the second plate are two studs located on the two lateral edges of the second plate and the female cooperation means of the core are two recesses made on the lateral edges of the core.

In accordance with another specific characteristic, the dimensions of each male cooperation means are slightly less than those of each female cooperation means so as to allow a slight clearance between the core and the second plate about the middle position of the core, corresponding to a centre of articulation of the prosthesis.

In accordance with another specific characteristic, the dimensions of each male cooperation means are substantially the same as those of each female cooperation means, so as to prevent any clearance between the core and the second plate and block the core in its middle position corresponding to a centre of articulation of the prosthesis.

In accordance with another specific characteristic, the cooperation means of the second plate are female means located in the vicinity of the edges of the second plate and cooperating with male means of the core.

In accordance with another specific characteristic, the dimensions of each male cooperation means are slightly less than those of each female cooperation means so as to allow slight clearance between the core and the second plate, about the middle position of the core, corresponding to a centre of articulation of the prosthesis.

In accordance with another specific characteristic, the dimensions of each male cooperation means are substantially the same as those of each female cooperation means so as to prevent any clearance between the core and the second plate and block the core at its middle position, corresponding to a centre of articulation of the prosthesis.

In accordance with another specific characteristic, the male cooperation means of the core are two studs located on the two lateral edges of the core and the female cooperation means of the second plate are four walls located, two by two, on each of the two lateral edges of the second plate.

In accordance with another specific characteristic, the female cooperation means of the second plate comprise a portion curved in to the centre of the plate and partially covering the male cooperation means of the core so as to prevent lifting of the core.

In accordance with another specific characteristic, the plane means representing the contact surfaces of the plates are substantially parallel or form an acute angle, the inclination obtained by such an angle allowing the overall form of the prosthesis to adapt to the anatomy of the backbone or optionally correct faults in inclination of the vertebrae of the patient for whom the prosthesis is intended.

In accordance with another specific characteristic, the same plates can be assembled with cores of different thicknesses and/or sizes and/or forms.

Another aim of the present invention is to eliminate certain disadvantages of the prior art by proposing instrumentation for insertion of an intervertebral disc prosthesis between the vertebrae allowing stability of the different elements of the prosthesis to be maintained between one another over the course of insertion of the latter between the vertebrae.

This aim is attained by insertion instrumentation of an intervertebral disc prosthesis between the vertebrae, comprising at least one prehension device for the prosthesis comprising a so-called manipulation end and a so-called prehension end, the prehension device being characterised in that it comprises a rod fitted, at the prehension end, with at least one axis of rotation on which are mounted at least two feet free in rotation about this axis, the ensemble of the rod and feet forming a clip mounted slidably in a hollow tube whereof the prehension end has an internal profile in a truncated form and comprises an axis perpendicular to the plane of the two feet of the clip, the ensemble formed by the two feet having a width, in the plane of the opening of the clip, greater than the width of the rod, the sliding of the rod in the tube, in the direction of the manipulation end, therefore causing closing of the clip by contact between the exterior of the feet and the truncated portion of the tube, the sliding of the rod in the tube, in the direction of the prehension end, causing opening of the clip by contact between the axis of the tube and the interior of the feet of the rod.

In accordance with another specific characteristic, the rod is fitted with a grip at the manipulation end, so as to allow the user to have the rod slide in the tube.

In accordance with another specific characteristic, the tube is fitted with a ring mobile in rotation relative to the tube and comprising a thread complementary to at least one threaded portion of the rod, the relative position of the thread of the ring and of the threading of the rod allowing blockage of the rod in the tube at least in the position where the clip is closed.

In accordance with another specific characteristic, the ends of the feet, at the level of the prehension end, each have at least one contact surface with at least an edge of an element of the prosthesis, imparting to the clip a profile adapted to the form of the prosthesis to be implanted.

In accordance with another specific characteristic, the profile adapted to the form of the prosthesis to be implanted consists of at least one contact surface with the leading edge of the prosthesis, at least one contact surface with the leading edge of a central core of the prosthesis and at least one contact surface with elements located on the lateral edges of the prosthesis.

In accordance with another specific characteristic, at least one contact surface with elements located on the lateral edges of the prosthesis consists of prehension means of cooperation means between the core and a plate of the prosthesis.

In accordance with another specific characteristic, at least one contact surface with elements located on the lateral edges of the prosthesis consists of cooperation means with a default form of at least one of the plates of the prosthesis.

In accordance with another specific characteristic, the profile adapted to the form of the prosthesis to be implanted consists of at least the contact surface with the leading edge of the prosthesis comprising 3 support faces complementary to 3 support faces present at least on the leading edge of at least one of the plates of the prosthesis, these 3 support faces comprising a leading face substantially perpendicular to the insertion axis of the prosthesis in the discal space and two antero-lateral faces each forming, in the plane of the plate, an angle with the leading face and with one of the lateral edges of the plate, the cooperation between this instrumentation profile and these 3 faces of the prosthesis allowing the latter to be stabilised during its insertion in the discal space.

BRIEF DESCRIPTION OF THE DRAWINGS

Other specific characteristics and advantages of the present invention will emerge more clearly from reading the description hereinbelow, given in reference to the attached diagrams, in which.

DETAILED DESCRIPTION OF THE EMBODIMENTS

The present invention relates to an intervertebral disc prosthesis comprising at least osseous anchoring means (41) forming a guide blade intended to prevent rotation of the plates of the prosthesis between one another and facilitate insertion of the prosthesis. More precisely, the prosthesis comprises at least first osseous anchoring means (42) and at least second osseous anchoring means (41), the first osseous anchoring means (42) extending to near the periphery of the plate on which it is situated and the second osseous anchoring means (41) being offset according to the antero-posterior axis relative to the first osseous anchoring means (42). The second offset osseous anchoring means (41) comprise a portion, so-called basal, solid with the plate on which it is situated and a portion, so-called sharp-edged, of width narrower than the basal portion. This sharp-edged portion forms a sort of blade intended to score the surfaces of the vertebral plates with which it comes into contact during implantation of the prosthesis and this blade then naturally forms a guide rail in the vertebra, thus preventing any displacement of the elements of the prosthesis between one another. In the various embodiments described hereinbelow, the prosthesis comprises at least two plates (1 and 2), so-called first (1) and second (2) plates, articulated between one another by means of a curved surface, so-called articulation surface, of at least one of the plates. This curved articulation surface allows pivoting of the plates (1, 2) relative to one another, by rotation about an axis substantially perpendicular to the plane of the plates and/or inclination of the plates (1, 2) relative to one another, by rotation about an axis substantially in the plane of the plates (1, 2). Each of the plates (1, 2) comprises a so-called contact surface intended to be made solid with a vertebral plate of one of the vertebrae between which the prosthesis is intended to be implanted. As is particularly evident in the embodiment illustrated in FIGS. 1A to 3C, the contact surface of the first plate (1) comprises a bulged portion (14) matching the form of the surface of the lower plate of a vertebra. The prostheses according to the present invention could comprise only two plates articulated between one another by means of a curved surface (not illustrated) or two plates (1, 2) articulated between one another by means of a central mobile core (3) having a curved surface cooperating with at least one part of a curved surface of one of the plates and a plane surface cooperating with at least one part of a plane surface of the other plate, as shown in FIGS. 1A to 2B.

In this illustrated embodiment, the first plate (1) comprises a curved articulation surface and this surface cooperates with at least one part of the curved surface of the core (3) to which it is complementary, to allow pivoting and/or inclination of the plates (1, 2) relative to one another. The plane surface of the core (3) cooperates with at least one part of a plane surface of the second plate (2) to allow translation of the core (3) relative to the second plate (2) in at least one direction perpendicular to the vertical axis of the spinal column and/or rotation of the core (3) relative to the second plate (2) by rotation about an axis substantially perpendicular to the plane of these plane surfaces. In the embodiments illustrated in the figures, the curved surface of the first plate (1) is concave and the curved surface of the core (3) is convex, but it could eventuate that the curved surface of the first plate (1) is convex and the curved surface of the core (3) is concave.

The second plate (2) comprises cooperation means (22) complementary to cooperation means (32) of the core (3) so as to limit or cancel at least this translation of the core (3) relative to the second plate (2). In the embodiments illustrated in the figures, the cooperation means (22) of the second plate (2) are male means located in the vicinity of the edges of the second plate (2) and cooperating with female means (32) of the core (3). In the embodiments illustrated in the figures, these male cooperation means (22) of the second plate (2) are two studs located on the two lateral edges of the second plate (2) and the female cooperation means (32) of the core (3) are two recesses made on the lateral edges of the core (3). In other possible embodiments not illustrated here, these cooperation means (32) of the core (3) can be male means consisting, for example, of two studs located on the two lateral edges of the core (3) and the cooperation means (22) of the second plate (2) can thus be female means consisting, for example, of four walls located, two by two, on each of the two lateral edges of the second plate (2). In these two embodiments, the cooperation means (22) of the second plate (2) can comprise a portion curved in towards the centre of the plate (2) and partially covering the cooperation means (32) of the core (3) so as to prevent lifting of the core (3). In an embodiment according to the present invention the dimensions of each male cooperation means (32, 22) could be slightly less than those of each female cooperation means (22, 32) so as to allow slight clearance between the core (3) and the second plate (2) about the middle position of the core (3) relative to the plates (1, 2), this middle position corresponding to a centre of articulation of the prosthesis. In another embodiment, the dimensions of each male cooperation means (32, 22) could be substantially identical to those of each female cooperation means (22, 32) so as to prevent any clearance between the core (3) and the second plate (2) and block the core (3) in its middle position corresponding to the centre of articulation. It can be interesting that the prosthesis according to the present invention can correct faults in inclination of the vertebrae between which it is intended to be implanted. In accordance with the desired result, this centre of articulation could have been provided to be at the centre of the prosthesis or be offset in at least one direction perpendicular to the axis of the spinal column. Similarly, the planes means representing the contact surfaces (14) of the plates (1, 2) could therefore be substantially parallel or form an acute angle. The inclination obtained by such an angle will allow the overall form of the prosthesis to adapt to the anatomy of the spinal column or optionally correct faults in inclination of the vertebrae of the patient for whom the prosthesis is intended. The same plates (1, 2) can be assembled with core (3) of different thicknesses and/or sizes and/or forms.

The prosthesis according to the present invention comprises osseous anchoring means ensuring good stability of the elements of the prosthesis between one another during implantation of the prosthesis between the vertebrae. For this, the prosthesis according to the present invention comprises at least first osseous anchoring means (42) and at least second osseous anchoring means (41). The first osseous anchoring means (42) extend to near the periphery of the plate on which it is situated and the second osseous anchoring means (41) is offset according to the antero-posterior axis relative to the first osseous anchoring means (42). Therefore, the first osseous anchoring means (42) could consist, in an embodiment not illustrated here, of a winglet oriented perpendicularly to the antero-posterior axis of the spinal column and located near the leading edge or posterior edge of the plate on which they are located. The second osseous anchoring means (41) will thus be located in the vicinity of the edge, respectively, trailing or leading. In the embodiment illustrated on FIGS. 1A to 4C, the first osseous anchoring means (42) consist of two winglets oriented as per the antero-posterior axis of the spinal column and located in the vicinity of the lateral edges of the plate on which they are found. These lateral winglets could have a length less than that of the plate and the second osseous anchoring means (41) could then be located in the vicinity of one of the trailing or leading edges of the plate. In these two embodiments, each of the winglets could be fitted with notches oriented so as to oppose withdrawal of the prosthesis from the discal space. In a variant embodiment, the notches of the first osseous anchoring means (42) are at a height increasing in the postero-anterior direction, as is particularly evident in FIG. 4C. More precisely, the notches are at a greater height at the front than at the rear of the prosthesis. Thus, during insertion, in the discal space, of the prosthesis in the antero-posterior direction of the vertebrae, each notch of the winglets attacks the osseous tissue not yet attacked by the preceding notch, thereby facilitating the insertion of the prosthesis in the discal space. The second offset osseous anchoring means (41) comprise a portion, so-called basal, solid with the plate on which it is situated and a portion, so-called sharp-edged, of a width narrower than the basal portion and forming a guide blade intended to prevent rotation of the plates of the prosthesis between one another and facilitate insertion of the prosthesis. This sharp-edged portion could be obtained, for example, due to at least one chamfer made on at least one of the lateral surfaces of the second osseous anchoring means (41). This second osseous anchoring means (41) could therefore consist, for example, of at least one aileron (41) or fin located in the vicinity of an edge of the plate and oriented in the insertion axis of the prosthesis between the vertebrae. Of course, two ailerons or fins could be provided to further still stabilise the prosthesis, even though the role of the aileron is more important on the posterior edge of the prosthesis, because the prosthesis is generally implanted along an antero-posterior pathway through the discal space between two adjacent vertebrae of the spinal column and this posterior edge is thus the first to be inserted in the discal space. In a variant embodiment, the aileron or fin could have a height less important at its posterior end than at its anterior end. Just as for the increasing height of the notches of the winglets, this difference in height of the aileron (41) gives it an inclined profile facilitating its insertion in the discal space in the antero-posterior direction. In addition, at least one of the plates (1, 2) of the prosthesis according to the present invention could, in an embodiment, comprise, at least on its trailing edge, at least one chamfer facilitating insertion of the prosthesis in the discal space.

Figure 1A:
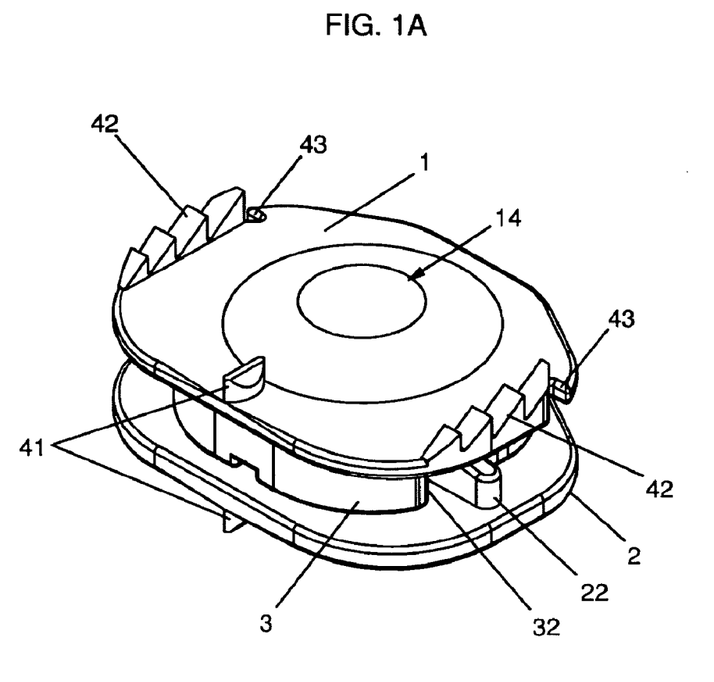
FIGS. 1A and 1B illustrate plan views in perspectives and, respectively, rear views and front views, of an intervertebral disc prosthesis according to an embodiment of the invention.
Figure 1B:
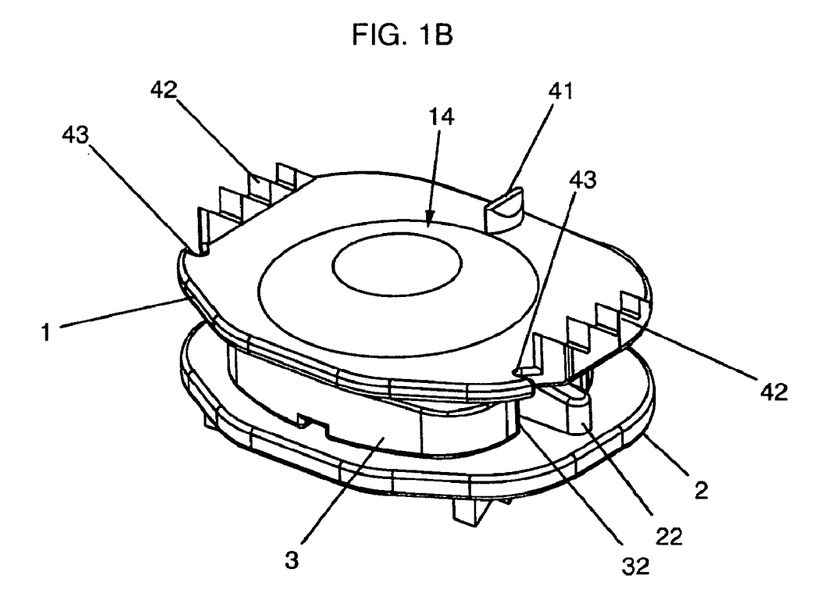
Figure 2A:
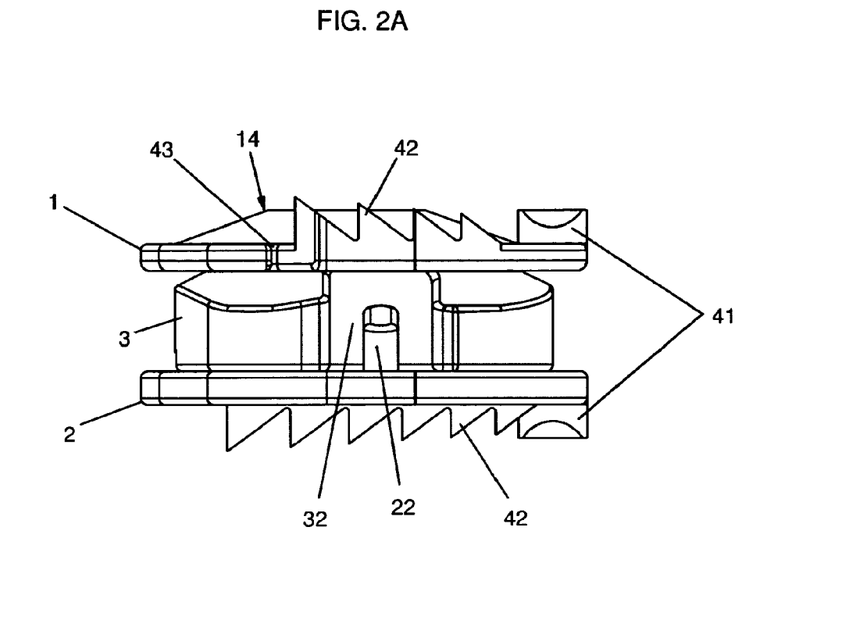
FIGS. 2A and 2B illustrate, respectively, a profile view and a rear view of an intervertebral disc prosthesis according to an embodiment of the invention.
Figure 2B:
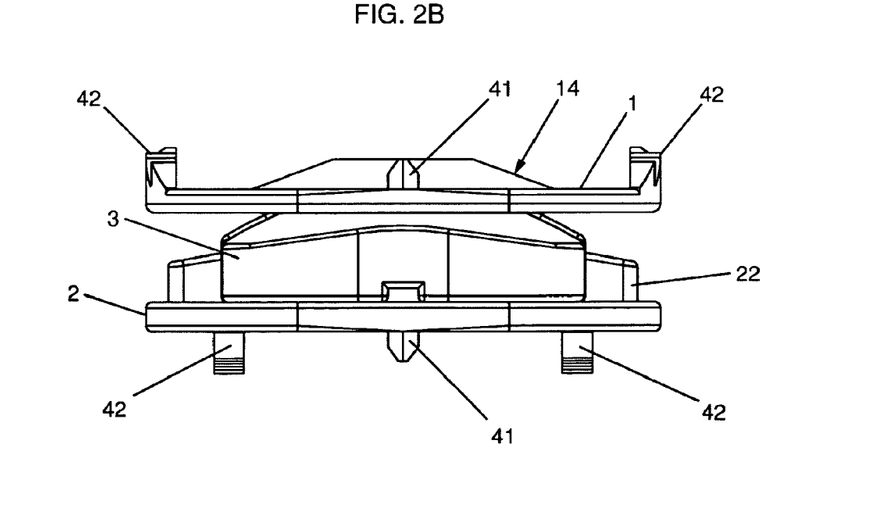
Figure 3A:
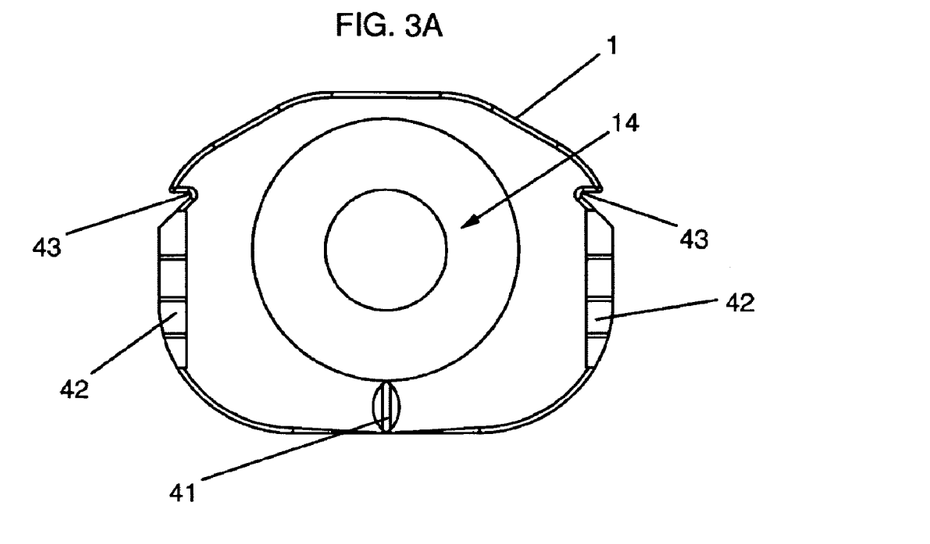
FIGS. 3A, 3B and 3C illustrate, respectively, a plan view, a rear view and a profile view of a first plate of an intervertebral disc prosthesis according to an embodiment of the invention.
Figure 3B:
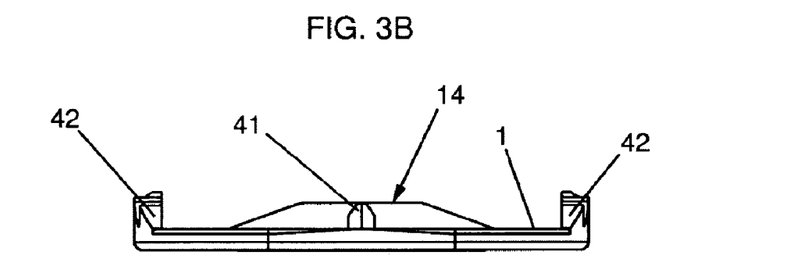
Figure 3C:
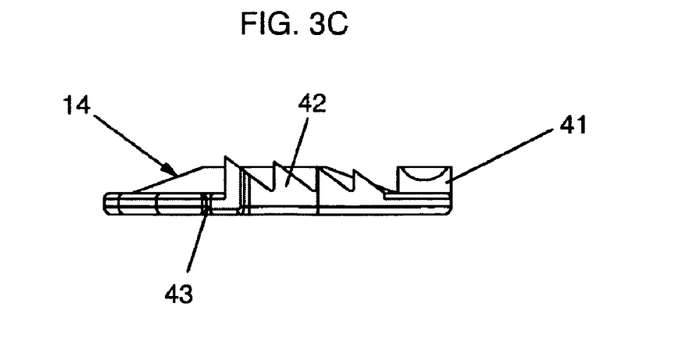
Figure 4A:
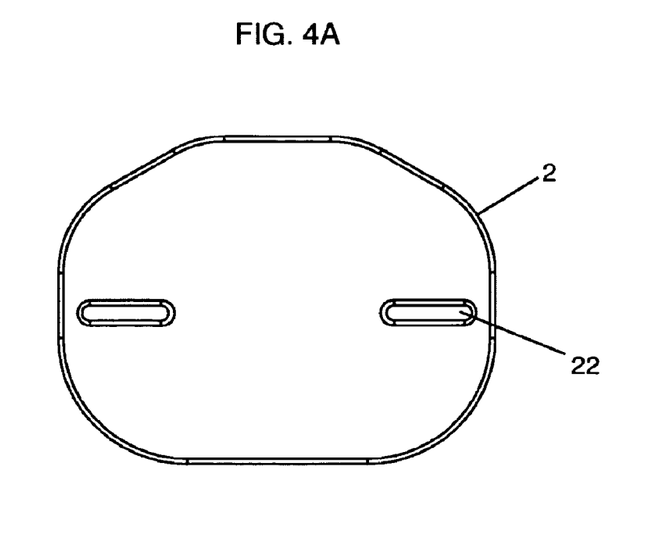
FIGS. 4A, 4B and 4C illustrate, respectively, a plan view, a rear view and a profile view of a second plate of an intervertebral disc prosthesis according to an embodiment of the invention.
Figure 4B:
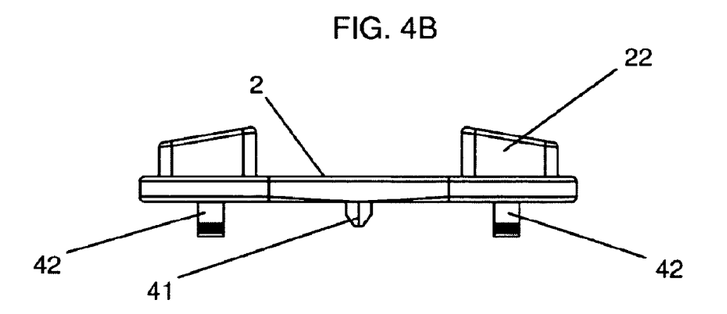
Figure 4C:
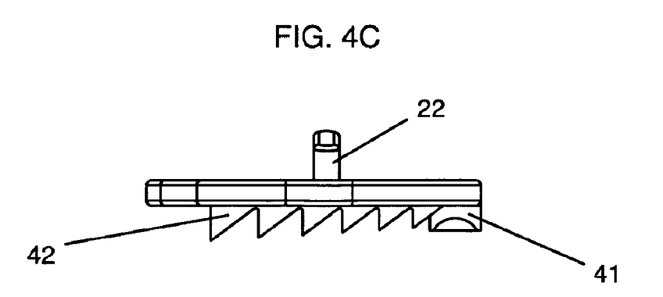
Figure 5A:
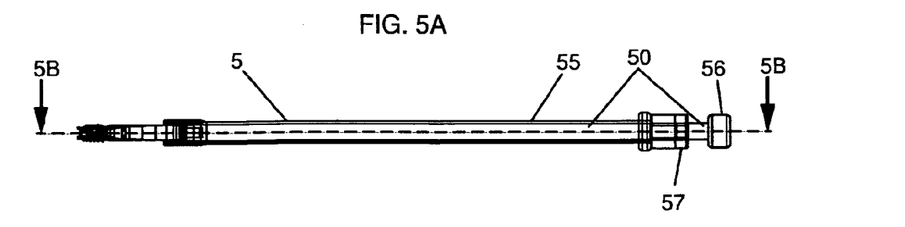
FIGS. 5A, 5B illustrate, respectively, a profile view with a cutting plane of FIG. 5C and a sectional view according to this plane, of a prehension device of a prosthesis according to an embodiment of the invention when the device is in the open position and does not lock in the prosthesis, FIGS. 5C and 5D representing a detail, respectively of the part 5C enclosed in FIG. 5B and of the part 5D enclosed in FIG. 5C, FIGS. 6A, 6B illustrate, respectively, a profile view with a cutting plane of FIG. 6B and a sectional view according to this plane, of a prehension device of a prosthesis according to an embodiment of the invention when the device is in the closed position and locks in the prosthesis, FIGS. 6C and 6D representing a detail, respectively of the enclosed part 6C in FIG. 6B and of the enclosed part 6D in FIG. 6C.
Figure 5B:
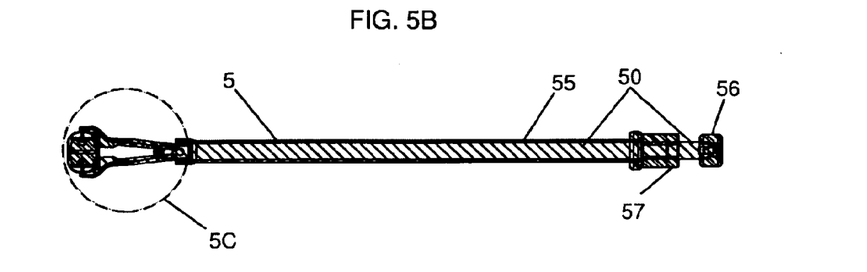
Figure 5C:
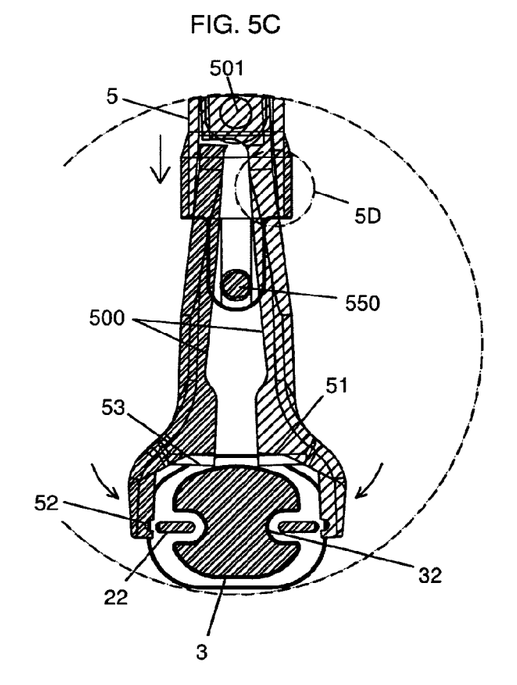
Figure 5D:
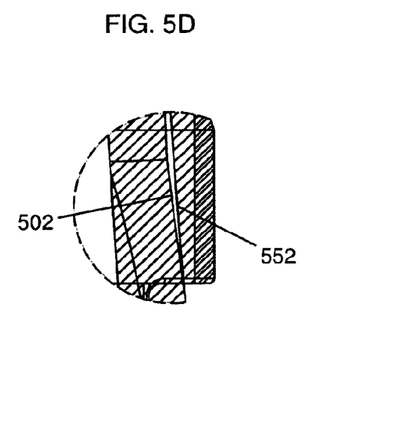
Figure 6A:
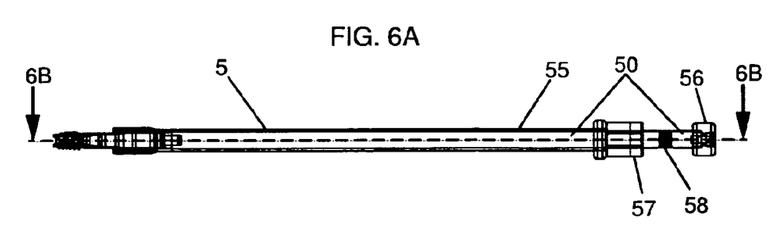
Figure 6B:
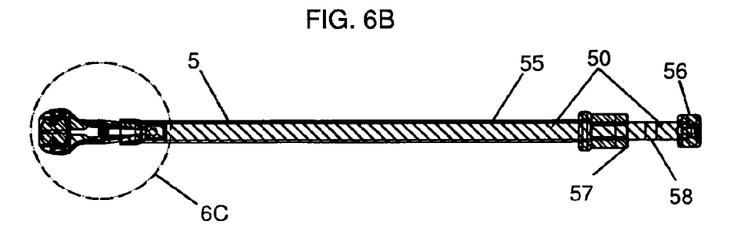
Figure 6C:
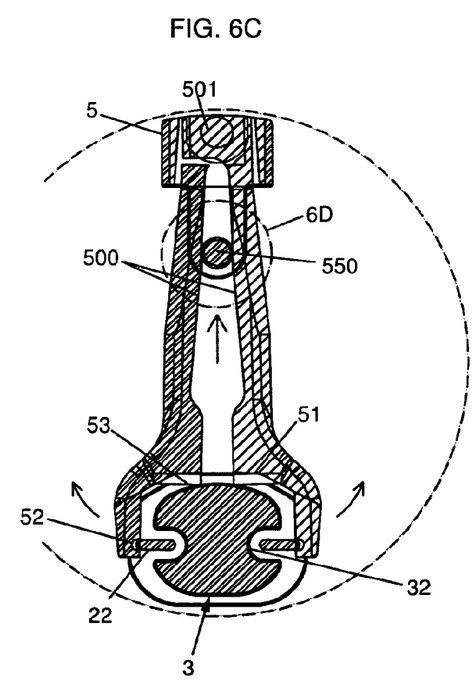
Figure 6D:
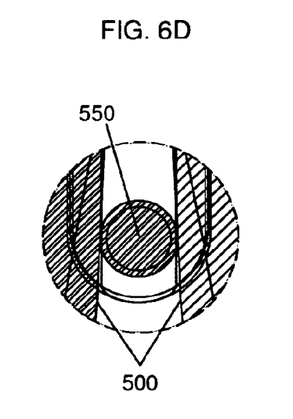

In an embodiment of the invention, at least the leading edge of at least one of the plates (1, 2) of the prosthesis could comprise 3 support faces, as is particularly evident in FIGS. 3A and 4A. These 3 faces consist of a leading face substantially perpendicular to the insertion axis of the prosthesis in the discal space and two antero-lateral faces each forming, in the plane of the plate, an angle with the leading face and with one of the lateral edges of the plate. Instead of presenting a rounded leading face, the prosthesis equipped with these 3 support faces is easy to stabilise during its insertion in the discal space, for example by means of an instrument whereof at least one portion has a form complementary to these 3 support faces. As is particularly evident in FIGS. 1A, 1B, 2A, 3A and 3C, at least one of the plates (1, 2) could comprise at least a default form (43), such as a notch, allowing the fitting of the end of a prehension device (5) of the prosthesis.

The invention further relates to instrumentation allowing insertion of the prosthesis between the vertebrae, ensuring good stability of the different elements of the prosthesis between one another during implantation. Such instrumentation according to the present invention comprises at least a prehension device (5) of the prosthesis, comprising a so-called manipulation end and a so-called prehension end. This prehension device (5) comprises a rod (50) fitted, at the prehension end, with at least an axis of rotation (501) on which are mounted at least two feet (500) free in rotation about this axis (501). The ensemble of the rod (50) and feet (500) forms a clip mounted slidably in a hollow tube (55) whereof the prehension end has an internal profile of truncated shape. The ensemble formed by the two feet (500) have a width, in the plane of the opening of the clip, greater than the width of the rod (50), so as to cooperate with the truncated portion of the hollow tube (55). The tube (55) comprises an axis (550) perpendicular to the plane of the two feet (500) of the clip and located between the two feet, so as to cooperate with the latter. The sliding of the rod (50) in the tube (55), in the direction of the manipulation end, therefore causes closing of the clip by contact between the exterior of the feet (500) and the truncated portion of the tube (55), while the sliding of the rod (50) in the tube (55), in the direction of the prehension end, causes opening of the clip by contact between the axis (550) of the tube (55) and the interior of the feet (500) of the rod (50). The rod (50) could be fitted with a grip (56) at the manipulation end, so as to allow the user to have the rod (50) slide in the tube (55). Also, this grip could be utilised to force insertion of the prosthesis in the discal space, for example, by striking on the grip by means of a tool such as a hammer, for example. The tube (55) could, in an embodiment of the invention, be fitted with a ring (57) mobile in rotation relative to the tube (55) and comprising a thread complementary to at least one threaded portion (58) of the rod (50). The relative position of the thread of the ring (57) and of the threading (58) of the rod (50) shall allow blockage of the rod (50) in the tube (55) at least in the position where the clip is closed. So, use of the prehension device (5) will help secure the clip on the prosthesis, for example while the surgeon strikes on the grip to insert the prosthesis in the discal space.

In the embodiment illustrated on the figures, the ends of the feet (500), at the level of the prehension end, each have at least one contact surface (51, 52, 53) with at least an edge of an element of the prosthesis, imparting to the clip a profile adapted to the form of the prosthesis to be implanted. This profile adapted to the form of the prosthesis to be implanted could consist of at least one contact surface (51) with the leading edge of the prosthesis, at least one contact surface (53) with the leading edge of a central core of the prosthesis and at least one contact surface (52) with elements located on the lateral edges of the prosthesis. In the case where the prosthesis comprises a central core fitted with cooperation means cooperating with cooperation means of at least one of the plates, the contact surface (52) with elements located on the lateral edges of the prosthesis could thus consist of prehension means of at least one of the cooperation means between the core (3) and a plate (1, 2) of the prosthesis. In the same way, in the case where the prosthesis comprises a plate having a default form (43), such as a notch, the contact surface (52) with elements located on the lateral edges of the prosthesis could consist of cooperation means with this default form (43). Also, the instrumentation according to the invention could be provided to cooperate perfectly with the different variant embodiments of the prosthesis according to the present invention and comprise a profile even more adapted to the form of the prosthesis. In particular, the contact surface (51) with the leading edge of the prosthesis, as well as optionally other surfaces, could comprise 3 support faces complementary to 3 support faces present at least on the leading edge of at least one of the plates (1, 2) of the prosthesis. These 3 support faces placed in complementary fashion to those of the prosthesis, then comprise a leading face substantially perpendicular to the insertion axis of the prosthesis in the discal space and two antero-lateral faces each forming, in the plane of the plate, an angle with the leading face and with one of the lateral edges of the plate. Cooperation between this instrumentation profile and these 3 faces of the prosthesis will help stabilise the latter during its insertion in the discal space, for example by preventing its rotation.

It must be evident for those skilled in the art that the present invention allows embodiments in numerous other specific forms without departing from the field of application of the invention as claimed. Consequently, the present embodiments must be considered by way of illustration, though they can be modified in the field defined by the reach of the attached claims, and the invention does not have to be limited to the details specified hereinabove.

The invention claimed is:

1. Instrumentation for inserting an intervertebral disc prosthesis between vertebrae of a spinal column comprising:
    a hollow tube having a manipulation end and a prehension end, the manipulation end having plural contact surfaces and a separation axis;
    a rod slidably disposed at least partially in the tube and having a manipulation end, a prehension end, a longitudinal axis, and a width;
    an axis of rotation attached to the rod proximal to the prehension end of the rod; and
    feet rotatable about the axis of rotation, the feet collectively forming a clip for grasping the intervertebral disc prosthesis, the clip having a width exceeding the width of the rod and having external feet surfaces and internal feet surfaces;
    in which sliding the rod in the tube in the direction of the manipulation end of the tube causes closing of the clip by contact between the exterior feet surfaces of the clip and the contact surfaces of the tube; and
    sliding the rod in the tube in the direction of the prehension end causes opening of the clip by contact between the separation axis of the tube and the interior feet surfaces.

2. Instrumentation for inserting an intervertebral disc prosthesis according to claim 1, in which the rod is fitted with a grip at the manipulation end.

3. Instrumentation for inserting an intervertebral disc prosthesis according to claim 1, in which the rod has threads in a threaded portion, and the tube is fitted with a ring rotatable about the tube and having a threaded portion with threads complementary to the threads of the rod, whereby movement of the rod in the tube is inhibited by engaging the threads of the rod with the threads of the ring.

4. Instrumentation for inserting an intervertebral disc prosthesis according to claim 1, in which the feet each have a feet contact surface complementary with a portion of a surface of the intervertebral disc prosthesis, which feet contact surfaces collectively form a clip profile having clip contact surfaces adapted to the profile of the intervertebral disc prosthesis.

5. Instrumentation according to claim 4 for inserting an intervertebral disc prosthesis having an edge surface, a core, and an element located on a lateral edge of the intervertebral disc prosthesis, in which the clip profile comprises:
    a clip contact surface complementary to the edge surface of the prosthesis;
    a clip contact surface complementary the core; and
    a clip contact surface complementary to the element located on a lateral edge of the prosthesis.

6. Instrumentation according to claim 5 for inserting an intervertebral disc prosthesis having a plate with a default form, in which the clip contact surface complementary to the element located on a lateral edge of the prosthesis is configured to complement the default form.

7. Instrumentation according to claim 4 for inserting an intervertebral disc prosthesis having a plate, a core, and cooperation means between the plate and the core disposed proximal to a lateral edge of intervertebral disc prosthesis, in which a clip contact surface is complementary to the cooperation means.

8. Instrumentation according to claim 4 for inserting an intervertebral disc prosthesis having an antero-posterior axis and an anterior edge portion comprising at least 3 support segments, one of which support segments is substantially perpendicular to the antero-posterior axis and two of which support segments each forms an angle with the support segment that is substantially perpendicular to the antero-posterior axis, in which the clip profile corresponds to the anterior edge portion.

* * * * *